(12) United States Patent
Sharifi-Mehr et al.

(10) Patent No.: US 10,813,678 B2
(45) Date of Patent: Oct. 27, 2020

(54) ROD CUTTING DEBRIS COLLECTOR AND GUIDE

(71) Applicant: Stryker European Holdings I, LLC, Kalamazoo, MI (US)

(72) Inventors: Amir Ali Sharifi-Mehr, Bloomingdale, NJ (US); Paul R. Rochette, Stanhope, NJ (US); Douglas G. Pedrick, Newburgh, NY (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 732 days.

(21) Appl. No.: 15/443,085

(22) Filed: Feb. 27, 2017

(65) Prior Publication Data

US 2017/0245907 A1     Aug. 31, 2017

Related U.S. Application Data

(60) Provisional application No. 62/301,152, filed on Feb. 29, 2016.

(51) Int. Cl.
*A61B 17/88*     (2006.01)
*B23D 59/00*     (2006.01)
(Continued)

(52) U.S. Cl.
CPC .......... *A61B 17/8863* (2013.01); *A61B 90/08* (2016.02); *B23D 59/006* (2013.01); *B23Q 11/0071* (2013.01); *B23Q 2240/007* (2013.01)

(58) Field of Classification Search
CPC .............. B23D 59/006; B23Q 11/0071; A61B 17/8863; A61B 90/08; A61B 2090/081; A47L 7/0095
See application file for complete search history.

(56) References Cited

U.S. PATENT DOCUMENTS

| 5,562,663 A | 10/1996 | Wisnewski et al. |
| 5,588,213 A * | 12/1996 | Swanberg ............ B23D 59/006 30/124 |

(Continued)

FOREIGN PATENT DOCUMENTS

| DE | 102006018976 B3 | 11/2007 |
| EP | 1722702 A1 | 11/2006 |

(Continued)

OTHER PUBLICATIONS

Extended European Search Report for Application No. EP17158141 dated Aug. 2, 2017.

*Primary Examiner* — Anu Ramana
(74) *Attorney, Agent, or Firm* — Lerner, David, Littenberg, Krumholz & Mentlik, LLP

(57) ABSTRACT

A debris collection device includes first and second members that are moveable relative to each other between first and second configurations. In the second configuration, the first and second members interface with each other and define a restraint opening that is configured to receive an elongate element, such as a spinal rod. The first and second members while in the second configuration define a guide opening that intersects the restraint opening. Such guide opening is configured to receive a cutting tool, such as a conical burr, drill bit, mill or saw. The first and second members have walls that, when in the second configuration, collectively define an interior space that has a volume sufficient to collect debris created by cutting the elongate element through the guide opening. Methods of utilizing the debris collection device allow for cutting of a spinal rod or the like in situ while capture debris caused by the cutting procedure.

16 Claims, 7 Drawing Sheets

(51) Int. Cl.
*B23Q 11/00* (2006.01)
*A61B 90/00* (2016.01)

(56) References Cited

U.S. PATENT DOCUMENTS

| | | | |
|---|---|---|---|
| 8,506,603 | B2 | 8/2013 | McClintock et al. |
| 8,968,420 | B2 | 3/2015 | Beale et al. |
| 10,105,025 | B2 * | 10/2018 | Lagimoniere, Jr. ... A47L 7/0095 |
| 2013/0103092 | A1 | 4/2013 | Ballard |

FOREIGN PATENT DOCUMENTS

| | | |
|---|---|---|
| NL | 8902959 A | 6/1991 |
| WO | 9916596 A1 | 4/1999 |
| WO | 9965415 A1 | 12/1999 |

* cited by examiner

ROD CUTTING DEBRIS COLLECTOR AND GUIDE

CROSS-REFERENCE TO RELATED APPLICATIONS

This application claims the benefit of the filing date of U.S. Provisional Patent Application No. 62/301,152, filed Feb. 29, 2016, the disclosure of which is hereby incorporated herein by reference.

BACKGROUND OF THE INVENTION

Spinal fusion procedures often utilize pedicle screws connected by rods in order to fuse multiple vertebrae with respect to each other. These pedicle screw assemblies may be utilized alone or in conjunction with one or more fusion implants. In many circumstances, such as in a revision procedure, it may be necessary to cut a previously implanted rod in situ. In situ rod cutting is typically performed by using bulky rod cutters that may be too large to safely access the rod within the patient without posing a risk to sensitive anatomy. For instance, one technique for rod cutting includes machining the rod in situ, such as by using a high speed burr. While effective for its intended purpose, such technique typically results in metal debris being showered into the patient's body. Therefore, further improvements are desirable.

BRIEF SUMMARY OF THE INVENTION

In one aspect of the present disclosure, a debris collection device includes a first member having a first opening extending entirely therethrough, and a second member moveable relative to the first member. The second member includes a catch basin at least partially defined by a base surface. The first and second members have a first configuration in which the second member is positioned relative to the first member so that an axis defined by the first opening intersects the base surface.

Additionally, the first and second members may be hingedly connected. The first and second members may also include a locking mechanism that locks the first and second members in the first configuration. Notches may extend into at least two opposing sidewalls of the first and second members such that when the first and second members are in the first configuration the notches are adjacently disposed to form a second opening. The axis of the first opening may be transverse to an axis of the second opening. Also, the first opening may be dimensioned to receive a cutting tool therein, and the second opening may be dimensioned to receive a spinal rod therein.

The first and second members may further have a second configuration in which end surfaces of the first and second members are spaced apart a distance sufficient to allow an elongate member to pass therebetween and into the notches of one of the first and second members. The elongate member may be a spinal rod. Also, when the first and second members are in the second configuration, the second member may be positioned relative to the first member such that the axis of the first opening does not intersect the base surface.

In another aspect of the present disclosure, a debris collection device includes a body having a first opening extending therethrough and a second opening extending therein. The first opening intersects the second opening and is dimensioned to receive an elongate member therein. The second opening terminates at a terminal end thereof within the body and is dimensioned to receive a cutting tool therein. The terminal end of the second opening is defined by a base surface and one or more interior sidewall surfaces extending from a perimeter of the base surface.

Additionally, the second opening may define an entrance into the body through an exterior surface thereof, and when the elongate member is received within the first opening, the base surface may be disposed at an opposite side of the elongate member than the entrance. The body may be comprised of a first member and a second member. The second member may include the base surface, and the second opening may extend entirely through the first member. The first and second members may be moveable relative to each other such that the first and second members have a first configuration in which first and second members are in a stacked arrangement, and second configuration in which the first and second members are in an unstacked arrangement. The first opening may be a circular opening defining semicircular notches within sidewalls of the first and second members. Also, the elongate member may be a spinal rod. The first and second members may be hingedly connected.

In a further aspect of the present disclosure, a surgical method of cutting an elongate element, includes connecting a first and second member of a debris collection device to an elongate element located within the body of a patient such that the elongate element is at least partially disposed between the first and second members; inserting a cutting tool through a first opening in the first member, the elongate member being exposed within the first opening; cutting the elongate member through the first opening; and collecting debris created by the cutting step within a catch basin of the second member.

Additionally, the catch basin may be defined by a base surface and at least one sidewall surface extending from a perimeter of the base surface. Also, the cutting step may include cutting the elongate member into first and second portions and the method may further include removing the first portion of the elongate member and the debris collection device from the second portion of the elongate member. During the removing step, the debris collection device may remain connected to the first portion of the elongate member.

BRIEF DESCRIPTION OF THE DRAWINGS

The features, aspects, and advantages of the present invention will become better understood in light of the following description, appended claims, and accompanying drawings in which:

DETAILED DESCRIPTION

Figure 1A:
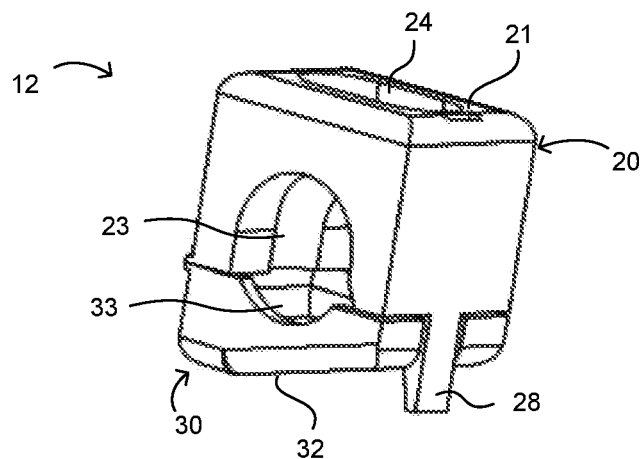
FIG. 1A is a front perspective view of a debris collection device in a first configuration according to an embodiment of the present disclosure.

As used herein, the terms "about," "generally," and "substantially" are intended to mean that slight deviations from absolute are included within the scope of the term so modified.

FIGS. 1A-1E depict a debris collection device 10 according to an embodiment of the present disclosure. As shown, device 10 generally includes a housing or body 12 comprised of a first member 20 and a second member 30. First member 20 includes first and second end surfaces 21, 22 defining first and second ends thereof. A second opening or guide opening 24 extends through first and second end surfaces 21, 22. Guide opening 24 is defined by interior sidewall surfaces 23 and is generally dimensioned to receive a cutting tool, such as a drill, high speed burr, reciprocating saw and the like. More particularly, interior sidewall surfaces 23 define the shape of opening 24 which is preferably an elongateshape, such as the capsule shape best shown in FIG. 1D. Other elongate shapes that may be implemented include, for instance, rectangular and ellipse. Such an elongate shaped opening 24 provides a cutting tool freedom of movement within the opening in one direction while being relatively constrained from movement in another direction. While an elongate shaped opening is preferable, symmetrical shapes, such as circular or a square, can also be implemented to form the general profile of opening 24.

In addition, guide opening 24 may include a compliant covering or flexible occluding material (not shown). For example, bristles, overlapping flexible polymer lips, a flexible polymer covering with a single slit, or the like may be attached to first member and at least partially cover opening 24. Such compliant covering is configured to conform to a cutting instrument inserted into opening 24 while also allowing such instrument to be moved about within opening 24. This helps prevent debris material from being discharged from opening 24, as well as may provide some tactile feedback to the surgeon during use.

Interior sidewall surfaces 23 in conjunction with exterior sidewall surfaces 25 define sidewalls that extend between first and second end surfaces 21, 22. Notches 26 extend into opposing sidewalls from second end 22 (best shown in FIG. 1B). These notches 26, as shown, are semi-circular. However, notches 26 may have other shapes, such as rectangular, triangular, and the like. Notches 26 are generally utilized to retain an elongate member, such as a spinal rod, therein. Thus, the shape of such notches 26 may depend on the shape of such elongate member.

Interior sidewalls 23 of first member 20 also define the shape of first member 20. As shown, first member 20 is generally rectangular and, thus, has four sidewalls. However, first member 20 can take on other shapes, such as a cylindrical or spherical shape in which first member 20 would have a single sidewall extending about opening 24.

Figure 1B:
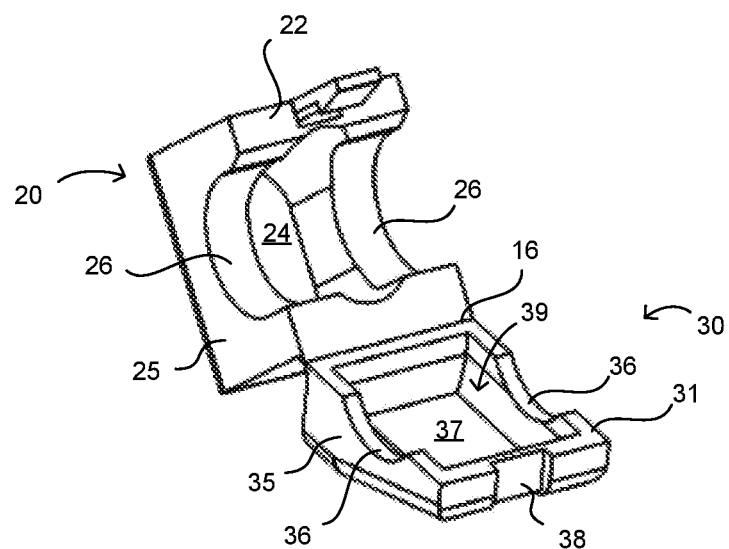
FIG. 1B is a front perspective view of the debris collection device of FIG. 1A in a second configuration.
Figure 1C:
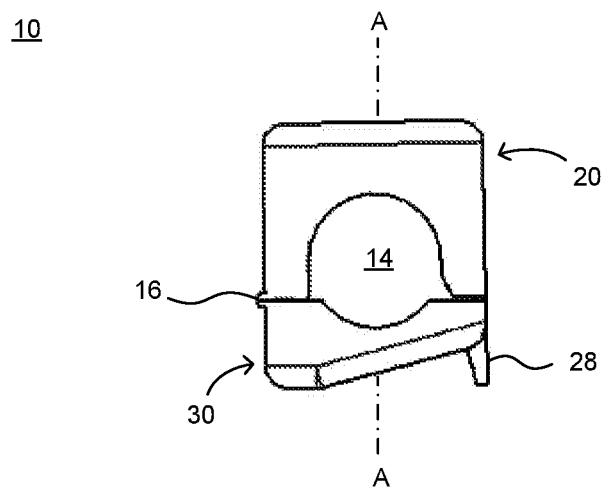
FIG. 1C is a side view of the debris collection device of FIG. 1A.
Figure 1D:
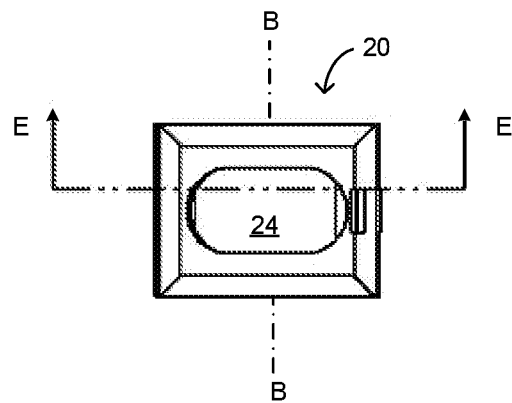
FIG. 1D is a top view of the debris collection device of FIG. 1A.
Figure 1E:
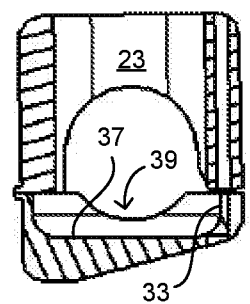
FIG. 1E is a cross-sectional view taken along line E-E of FIG. 1D.

Second member 30 includes first and second end surfaces 31, 32 defining first and second ends thereof. An opening extends through first end surface 31 and terminates prior to reaching the second end. Such opening forms a catch basin 39 which is defined by interior sidewall surfaces 33 and a base surface 37 that extend between sidewall surfaces 33. Sidewall surfaces 33 extend from a perimeter of base surface 37. Catch basin 39, as shown in FIG. 1B, is generally square shaped. However, catch basin 39, may have other shapes, such as a circular shape. Catch basin 39 may have a larger perimeter than guide opening 24 to help facilitate accumulation of debris. However, in some embodiments, catch basin 39 may have the same perimeter as guide opening 24.

Interior sidewall surfaces 33 in conjunction with exterior sidewall surfaces 35 define sidewalls that extend between first and second end surfaces 31, 32. Notches 36 extend into opposing sidewalls from the first end surface 31. These notches 36, as shown, are circular. However, notches 36 may have other shapes, such as rectangular, triangular, and the like, and are generally shaped to correspond with notches 26 of first member 20 so as to conform to an elongate member, as described below.

First and Second Configurations

First and second members 20, 30 are hingedly connected by a hinge 16. First and second members 20, 30 also include a locking mechanism that comprises a latch 28 cantilevered to first member 20 and a corresponding groove 38 extending into second member 30. In this regard, first and second members 20, 30 have a first configuration and a second configuration. In the first configuration (depicted in FIG. 1A), first and second members 20, 30 are in a stacked arrangement such that second end surface 22 of the first member abuts or is placed adjacent to first end surface 31 of second member 30. In addition, guide opening 24 of first member 20 communicates with catch basin 39 such that an axis A-A (see FIG. 1C) defined by guide opening 24 intersects base surface 37. Also, latch 28 extends through groove 38 and connects to second member 30 in a locking fashion.

Also, in this configuration, notches 26, 36 of first and second members 20, 30 form a first opening or restraint opening 14 (best shown in FIG. 1C) that extends entirely through body 12. Restraint opening 14 intersects guide opening 24 such that axis A-A is transverse to an axis B-B (see FIG. 1D) defined by restraint opening 14. Moreover, restraint opening 14 is dimensioned to receive an elongate member therein, such as a spinal rod. More particularly, opening 14 is dimensioned so as to clamp an elongate member therein between first and second members 20, 30 and restrain debris collection device 10 from movement by such clamping. Thus, in one embodiment, opening 14 may be dimensioned to receive a single size elongate member.

However, in another embodiment, flexible gaskets or the like may line notches 26, 36 so that debris collection device 10 can be attached to several different sized elongate members and to provide a tight seal against an elongate member so as to help prevent device 10 from rotating about such elongate member when connected thereto. These gaskets or the like may also aid in preventing debris from being discharged from device 10. In yet another embodiment, restraint opening 14 may have a larger dimension at one side of body 12 than another side of body 12 so that only the smaller side clamps an elongate member. This allows an elongate member to be cut into two distinct portions and for debris collection device 10 to be removed from an unclamped portion without the need to unlock the locking mechanism.

In the second configuration (depicted in FIG. 1B), latch 28 is disconnected from second member 30 and first and second members 20, 30 are rotated away from each other about hinge 16. In this regard, second end surface 22 of first member 20 and first end surface 31 of second member 30 are separated so that first and second members 20, 30 are no longer in their stacked arrangement. In addition, second end surface 22 and first end surface 31 are spaced a sufficient distance as to allow an elongate member to pass therebetween and into or out of notches 26 or notches 36. Furthermore, axis A-A may not intersect base surface 37.

Debris collection device 10 is preferably made from a biocompatible metallic material, such as stainless steel, titanium, niobium, cobalt-chromium, and the like. However, debris collection device 10 can also be made from a biocompatible polymer material, such as polyether ether ketone (PEEK) and the like. In some embodiments, first and second member 20, 30 may be made from different materials. For example, second member 30 may be made from a harder material than first member so as to prevent a high speed burr or other device from cutting through second member 30. In addition, debris collection device 10 may be disposable, or may be reusable and, therefore, may also be sterilizable.

Figure 2:
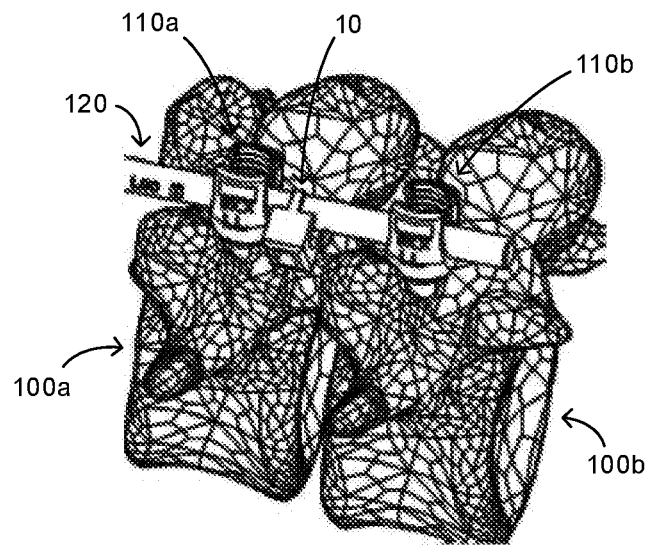
FIGS. 2-5 illustrate a method of rod cutting using the debris collection device of FIG. 1A according to an embodiment of the present disclosure.

FIGS. 2-5 depict a method of cutting an elongate element in situ and collecting debris generated therefrom. In the method, an incision is made exposing the patient's spine. A spinal rod 120 may be already connected to adjacent vertebrae 100a-b via pedicle screws 110a-b, such as in a revision procedure, or such spinal rod 120 may be connected to vertebrae 100a-b once vertebrae are accessed. In the procedure depicted, spinal rod 120 is designated for separation at a location between pedicle screws 110a-b. In this regard, debris collection device 10 is connected to rod 120 at the designated location, as shown in FIG. 2. This is achieved by moving first and second members 20, 30 into the second configuration and placing rod 120 into notches 26 or notches 36. First and second members 20, 30 are then moved into the first configuration about rod 120 so that rod 120 is clamped between first and second members 20, 30 and disposed within restraint opening 14. This is done so that guide opening 24 generally is directed upward so that debris falls downward away from opening 24. In the first configuration, latch 28 is locked to second member 30 and device 10 is restrained to rod 120. In other procedures, it is possible for debris collection device 10 to be connected to rod 120 at other points, for instance, to cut a portion of the rod extending past a pedicle screw and not to another such screw.

Figure 3:
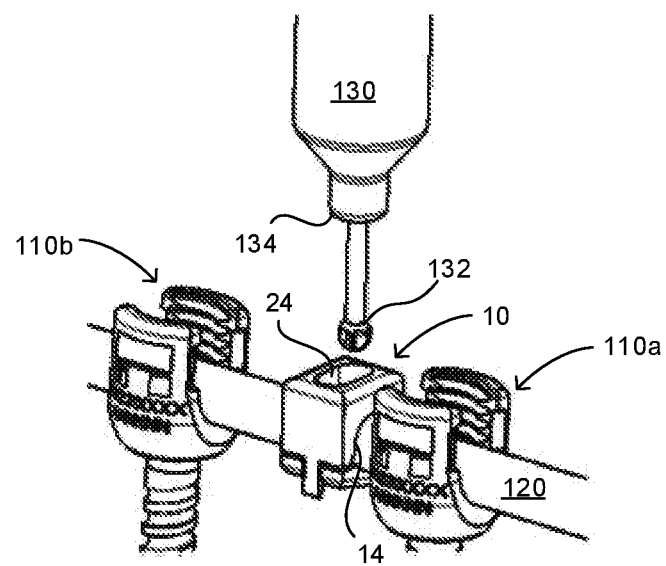
Figure 4:
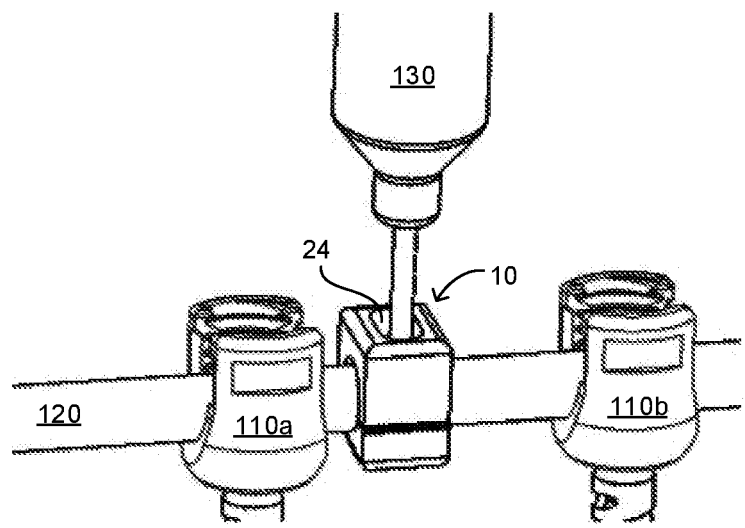

Once debris collecting device 10 is connected to rod 120, a cutting device 130, such as high speed burr 130, is inserted into guide opening 24, as shown in FIGS. 3 and 4. More particularly, cutting head 132 is inserted into opening 24 and is placed against rod 120. With instrument 130 turned on, cutting head 132 is moved back and forth within opening 24 along the widest portion of opening 24 which is positioned transverse to an axis of rod 120. As cutting head 132 cuts through rod 120, debris is formed which falls into catch basin 39, which is disposed at an opposite side of rod 120 than the entrance to opening 24. Interior sidewalls 23 of first member helps prevent debris from being thrown out of device 10, and the shape of opening 24 helps guide cutting head 132 to form an evenly cut surface. It is noted that opening 24 may be fitted with a compliant material, such as the gasket or bristles describe above, that allows insertion of cutting head 132 but thereafter forms around the cutting implement. This can prevent material from being thrown out of opening 24 as well. As rod 120 is cut, a shoulder 134 of instrument 130 (see FIG. 3) may abut first end 21 or interfere with opening 24 to prevent cutting head 132 from cutting through second member 30. In other words, shoulder 134 may act as a depth stop limiting over penetration and indicating to an operator when rod 120 is completely severed.

Figure 5:
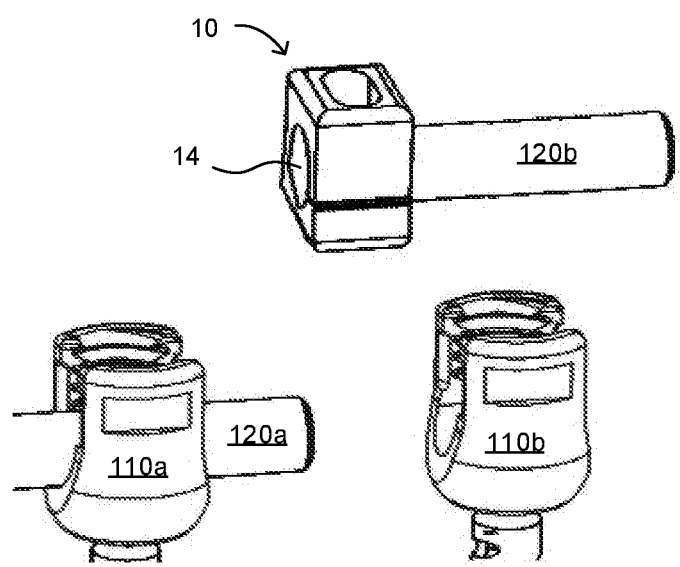

Once the rod 120 is completely cut into first and second portions 120a-b, the second portion 120b is removed, as shown in FIG. 5. In particular, second portion 120b is released from pedicle screw 110b, and device 10 is released from first portion 120a. Second portion 120b, with device 10 remaining connected thereto, is removed from the patient, thereby also removing the debris formed from the cutting procedure. Thereafter, latch 28 may be released and first and second members 20, 30 returned to the second configuration so that the debris can be discarded and device 10 can be utilized again. Alternatively, device 10 may be discarded along with the debris.

Numerous variations and combination of the features discussed above can be utilized without departing from the present invention. For example, first and second members are described above as being hingedly connected. However, in some embodiments, first and second members may be entirely separated but may be connectable over an elongate member, such as rod 120, via a locking mechanism. Such locking mechanism can include a snap-fit mechanism, ball-detent mechanism, or ratchet mechanism, for example. In addition, device 10 may include a handle (not shown) extending from one or both of the first and second members 20, 30 to allow an operator to control device 10 while cutting an elongate member therethrough.

FIG. 6A-6D depict a debris collection assembly 200 according to another embodiment of the present disclosure. Assembly 200 generally includes a holding instrument 240 and a debris collection device 210. Holding instrument 240 in the depicted embodiment is a forceps that includes first and second arms 242, 243 connected at a pivot axis 244. First and second arms 242, 243 each include ratchet members 246a-b extending therefrom that are configured to interface with each other to form a locking mechanism that is capable of locking arms 242, 243 in a relative position.

Debris collection device 210 is connected to holding instrument 240. In this regard, a first member 220 of debris collection device 210 is connected to an end of first arm 242, and a second member 230 of debris collection device 210 is connected to an end of second arm 243. Debris collection device 210 is similar to debris collection device 10 in that it has a clamshell construction of two corresponding members 220, 230 that are configured to be clamped over an elongate element and that define a guide opening 216 for guiding a cutting tool 250 to cut the elongate element. However, debris collection device 210 differs in that the first and second members 220, 230 interface vertically to form an interior space 218 for debris collection rather than horizontally. In other words, first and second members 220, 230 of debris collection device 210 have a vertical interface that extends in a vertical plane, whereas first and second members 20, 30 of debris collection device 10 have a horizontal interface that extends in a horizontal plane.

In this regard, first member 220 of debris collection device 210 includes an upper wall, ceiling, or first transverse wall 221 and a lower wall, floor or second transverse wall 222. Sidewalls 225 extend between the upper and lower walls 221, 22 so that at least one side of first member 220 is open. Stated another way, one or more sidewalls 225 extend between upper and lower walls 221, 222 and partially about a perimeter defined by the upper and lower walls 221, 222 thereby defining a side-opening 227 that extends into a space defined between upper and lower walls 221, 222 (best shown in FIG. 6A). Semicircular notch 228 extends into upper wall 221, and semicircular notch 226 extends into the one or more sidewalls 225 adjacent side-opening 227 of first member 220. However, no notches extend into lower wall 222.

Figure 6A:
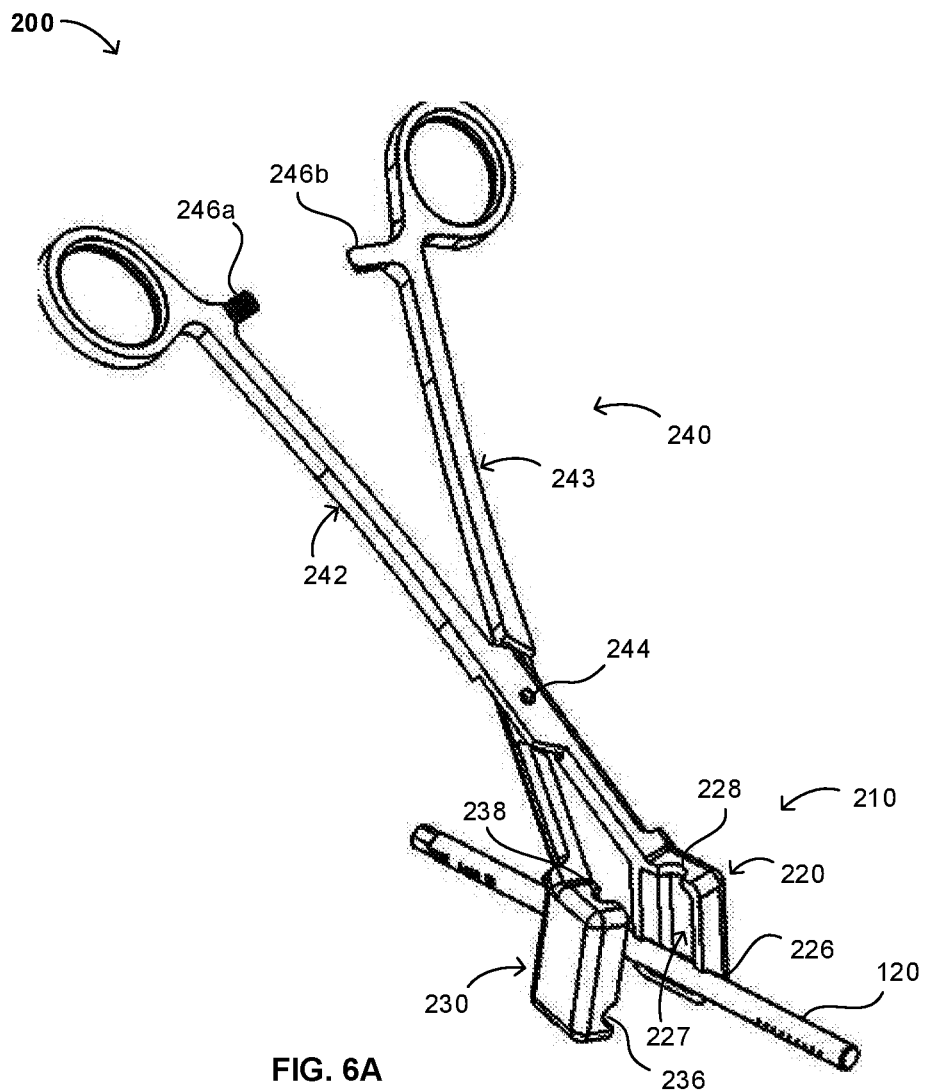
FIG. 6A is a perspective view of a debris collection assembly including an manipulation instrument and debris collection device according to a further embodiment of the present disclosure in a first configuration relative to an elongate rod.
Figure 6B:
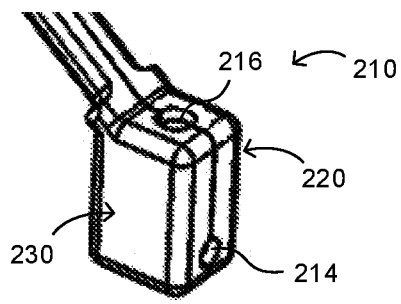
FIG. 6B is an enhanced view of the debris collection device of FIG. 6A in a second configuration.

Second member 230 is similarly configured with an upper wall 231, lower wall 232, sidewalls 235, and notches 236, 238 so that when the first and second members 220, 230 interface, the respective notches 226, 236, 228, 238 of first and second members 220, 230 align to form a guide opening 216 and restraint opening 214, as best shown in FIG. 6B. In this regard, debris collection device 210 has a first configuration and a second configuration. In the first configuration, shown in FIG. 6A, first and second arms 242, 243 are pivoted relative to each other so that first and second members 220, 230 disposed at ends thereof do not touch. In the second configuration, shown in FIG. 6B, first and second arms 242, 243 are pivoted relative to each other so that the side-openings of the respective members 220 and 230 face each other and upper walls 221, 231, lower walls 222, 232, and sidewalls 225, 235 respectively contact each other to form an enclosed interior space or catch basin 218 and a seal that prohibits material gathered within interior space 218 from escaping therefrom. Such seal may be further enhanced by a gasket or tongue and groove feature at the interface. In the second configuration, notches 226 and 236 and notches 228 and 238 align to respectively form restraint and guide openings 214, 216. Restraint opening 214 extends entirely through debris collection device 210 while guide opening 216 does not. In other words, guide opening 216 only extends through the respective upper walls 221, 231 of first and second members 220, 230, but not through lower walls 222, 232. However, restraint opening 214 and guide opening 216 each define respective axes that intersect each other.

Restraint opening 214, as shown, is substantially circular to correspond to a circular rod. However, such opening 214 can have various different shapes to match the geometry of a corresponding elongate member. For example, opening 214 can be rectangular or triangular. In addition, opening 214 may have a compliant material lining said opening 214 so as to be capable of conforming to elongate members of differing cross-sectional dimensions.

Also, as shown, guide opening 216 is substantially circular. This differs from guide opening 24 of debris collection device 10. As previously described, debris collection device 10 has a capsule or ovular shaped guide opening 24 which is configured to receive a conical burr cutting instrument 130. Such ovular shape allows the burr instrument 130 to be moved in a sweeping motion to cut an elongate element clamped by collection device 10. However, the circular shape of guide opening 216 is configured to receive a drill bit or axial cutting tool 250. Axial cutting tool 250 is depicted in FIG. 6B and has a shaft 252 and a cutting portion 254 at the end of shaft 252. Cutting portion 254 is configured to cut through an elongate element, such as a spinal fixation rod, while tool 250 is advanced in an axial direction. Thus, guide opening 216 of device 200 is configured to constrain tool 250 to axial movement and to guide tool 250 toward an elongate element disposed within restraint opening 214. However, it should be understood that device 200 could include the ovular opening 24 of device 10 so that device 210 could guide tool 130.

As mentioned, axial cutting tool 250 may be a drill bit that includes a shaft 252 and cutting portion 254 at the end of shaft 252. Cutting portion 254 generally has a length that is less than a distance between guide opening 216 and restraint opening 214. This helps ensure that the entirety of cutting portion 254 is disposed within interior space 218 during cutting. This helps prevent debris material from being guided along flutes of cutting portion 254 and out of guide opening 216. To further help block debris material from being inadvertently transported by cutting tool 250 out of guide opening 216, shaft 252 may have an outer diameter greater than an outer diameter of cutting portion 254. Alternatively, cutting tool 250 may have a bushing disposed over shaft 252. In this regard, the larger diameter of shaft 252 or bushing creates a shoulder (not shown) that can block debris material axially transported by the flutes of cutting portion 254 from travelling any further axially than the shoulder. Axial cutting tool 250 may also have indicia disposed along its shaft 252 to indicate the depth of tool 250 within collection device 210. For example, a first indicia line may indicate when cutting tool 250 contacts an elongate member within device 210, and a second indicia line that indicates when cutting tool 250 has cut entirely through the elongate member.

Figure 6C:
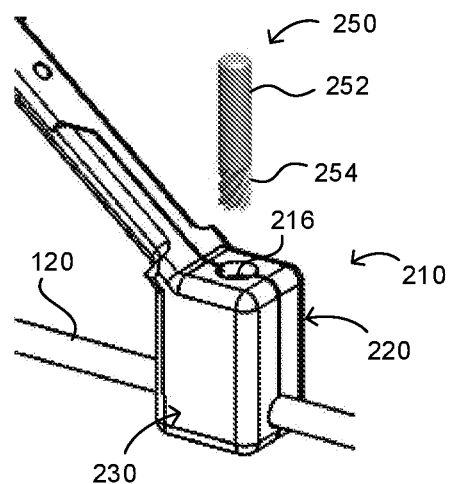
FIG. 6C is an enhanced view of a cutting tool and the debris collection device of FIG. 6A in the second configuration over an elongate rod.
Figure 6D:
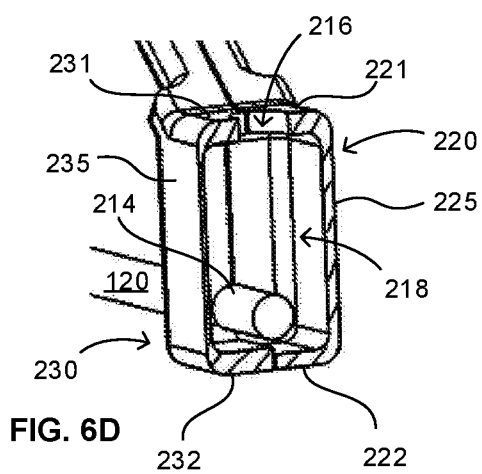
FIG. 6D is a sectional view of the debris collection device and elongate rod of FIG. 6C taken along a midline thereof.

In a method of using instrument 200, an incision is made exposing the patient's spine. A spinal rod 120 may be already connected to adjacent vertebrae via pedicle screws, such as in a revision procedure, or such spinal rod 120 may be connected to vertebrae once the vertebrae are accessed. In the procedure, spinal rod 120 is designated for separation at a location between pedicle screws (not shown). In this regard, debris collection device 210 is connected to rod 120 at the designated location, as shown in FIG. 6C. This is achieved by moving first and second members 220, 230 into the first configuration by pivoting arms 242 and 243 about pivot axis 244 and placing rod 120 into notches 226 or notches 236, as shown in FIG. 6A. First and second arms 242, 243 are then pivoted into the second configuration so that rod 120 is clamped between first and second members 220, 230 and disposed within restraint opening 214, as best shown in FIGS. 6C and 6D. This is done so that guide opening 216 generally is directed upward so that debris falls downward away from opening 216. As debris collection device 210 is moved into the second configuration, ratchet members 246a-b engage to lock first and second members 242, 243 into position over rod 120.

Once debris collecting device 210 is connected to rod 120, a cutting tool 250 is inserted into guide opening 216. More particularly, cutting tool 250 is advanced axially through guide opening 216 and into contact with rod 120. With tool 250 turned on, cutting portion 254 is advanced axially through rod 120. As tool 250 cuts through rod 120, debris is formed which is gathered in interior space 218 (see FIG. 6D). It is noted that opening 216 may be fitted with a compliant material, such as a gasket or bristles that allows insertion of cutting portion 250 but thereafter forms around the cutting implement. This can further help prevent material from being advanced out of opening 216. Tool 250 may have a depth stop (not shown) that prevents tool 250 from being advanced too far.

Once rod 120 is completely cut, assembly 200, debris, and the free segment of rod 120 can be removed from the patient. Thereafter, locking mechanism 246a-b may be released and first and second members 220, 230 returned to the first configuration so that the debris can be discarded and device 210 utilized again. Alternatively, where device 210 is modularly connected to arms (as discussed above), device 210 may be discarded along with the debris. As shown, debris collection device 210 of assembly 200 is integral with holding instrument 240. In other words, first arm 242 and first member 220 are a monolithic structure as is second arm 243 and second member 230. However, in some embodiment debris collection device 240 may be a modular component connectable to instrument 240. For example, first member 220 of debris collection device 200 may be connectable to first arm 242, and second member 230 may be connectable to second arm 243. In this regard, first and second arms 242, 243 may be specially adapted for connection to respective first and second members 220, 230. However, in other embodiments, first and second members 220, 230 may be adapted to be connected to standard forceps, vise grips, or any other clamping/holding instrument known in the art. For example, first and second members 220, 230 may include extensions (not shown) that extend from sidewalls thereof and are configured to connect to an end of a standard pair of surgical forceps. For instance, first and second members 220, 230 may be injection molded plastic that may have features that are configured to snap onto ends of a standard holding instrument.

Various kits of the above mentioned devices, tools, instruments and assemblies can be provided, for example, to a surgical theater for performing the previously described method. For example, in one embodiment, a kit may include holding instrument 240, debris collection device 210, and cutting tool 250. In another embodiment, a kit may only include debris collection device 210 and cutting tool 250. In a further embodiment, the previously described kits may include a plurality of debris collection devices 210 each having different sized restraint openings 214 to accommodate different sized elongate members. In other embodiments, the kits may include a plurality of virtually identical debris collection devices 210 where each debris collection device 210 is disposable.

In even further embodiments, each of the described kits may include a plurality of different cutting tools and a plurality of debris collection devices each with different guide openings configured to receive a different cutting tool. For example, a kit may include a first cutting tool and a first debris collection device that has a guide opening configured for the first tool, a second cutting tool and a second debris collection device that has a guide opening configured for the second cutting tool, and third instrument and a third debris collection device that has a guide opening configured for the third cutting tool. In this example, the first tool may be conical burr 130, the second instrument may be drill bit 250, and the third tool may be a saw blade (not shown). Correspondingly, the guide opening of the first debris collection device may be an elongate opening like that of opening 24, the guide opening of the second debris collection device may be a cylindrical opening like that of opening 216, and the guide opening of the third debris collection device may be a narrow slot configured to receive the saw blade. This provides the operator flexibility to select an appropriate cutting tool based on the circumstances.

In still further kit embodiments, a plurality of different sized cutting tools 250 and a plurality of different sized sleeves or bushings (not shown) for said cutting tools 250 may be provided in one of the aforementioned kits. For example, assembly 200 may be used to cut elongate elements of various sizes. In this regard, guide opening 216 may be much larger relative to the diameter of most or all of the cutting tools 250 in the kit so as to be able to accommodate the various sized cutting tools 250. Thus, to allow each different sized cutting tool 250 to snugly fit within opening 216, corresponding bushings may be provided in the kit that each have the same outside dimensions, but have differing inside dimensions to accommodate its respective cutting tool 250. Alternatively, rather than sleeves/bushings, each cutting tool 250 may have a portion of its shaft 252 the same size as all the other cutting tools 250 but with different sized cutting portions 254 which are particularly configured to cut a correspondingly sized elongate element. In this regard, the shaft 252 of each cutting tool 250 in the kit could slidably and rotatably engage the guide opening 216 while having different sized cutting portions 254.

Figure 7A:
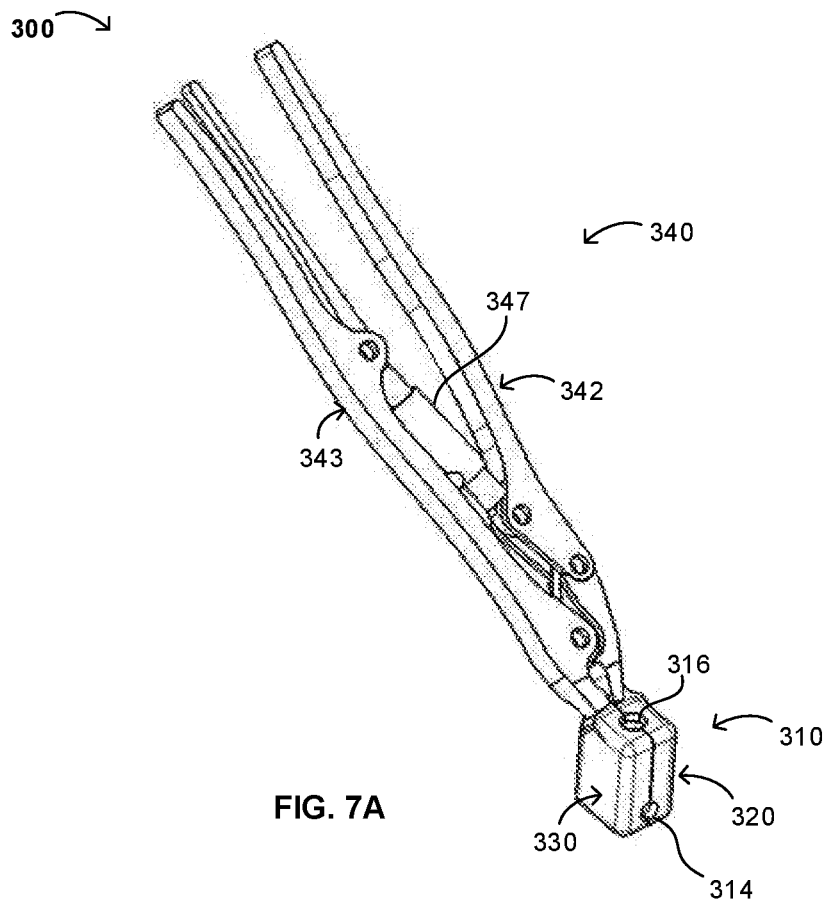
FIG. 7A is a perspective view of a debris collection assembly according to a further embodiment of the present disclosure.
Figure 7B:
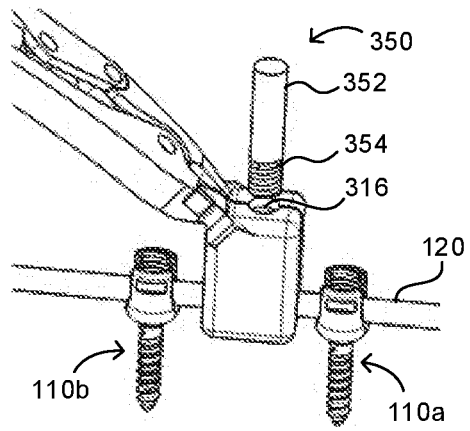
FIG. 7B is an enhanced view of a cutting tool and a debris collection device of the assembly of FIG. 7A clamped over an elongate rod that has a plurality of pedicle screws connected thereto.
Figure 7C:
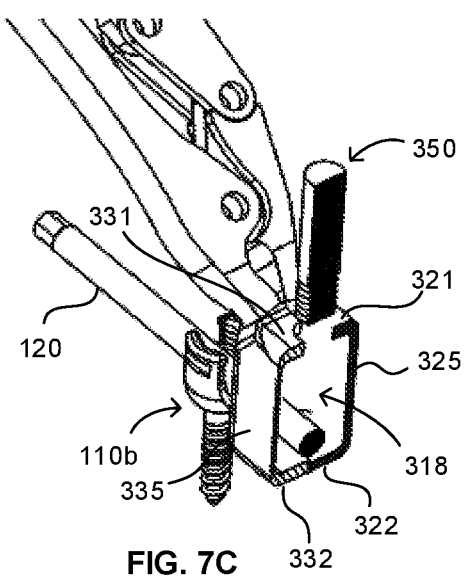
FIG. 7C is a sectional view of the cutting tool, debris collection device, and elongate rod of FIG. 7B taken along a midline thereof.

FIGS. 7A-7C depict a debris collection assembly 300 according to another embodiment of the present disclosure. Assembly 300 is similar to assembly 200 in that it includes a holding instrument 340 and a debris collection device 310. However, assembly 300 differs with regard to holding instrument 340. In this regard, holding instrument 340, instead of being forceps like instrument 240, is a vise grip that includes a first arm assembly 342, a second arm assembly 343 and an adjustable locking member 347. First and second arm assemblies 342, 343 are pivotably connected to each other, and adjustable locking member 347 is pivotably connected to both the first and second arm assemblies 342, 343. In addition adjustable locking member 347 is adjustable to create a toggle lock as is known in the art that locks the first and second arm assemblies 342, 343 in a select position relative to each other.

Debris collection device 320 is connected to holding instrument 340. In particular, a first member 320 of debris collection device 320 is connected to first arm assembly 342, and a second member 330 is connected to second arm assembly 343. First and second members 342, 343 are similar to members 220 and 230 in that they each have upper walls 321 and 331, lower walls 322 and 332, sidewalls 325 and 335, and notches. Additionally, first and second members 320, 330 have a first and second configuration wherein in the second configuration, said walls and notches interface to form an interior space 318 for debris collection, a restraint opening 314 for restraining an elongate member, and a guide opening 316 for guiding a cutting tool 350 into interior space 318 to cut an elongate element partially disposed therein. A method of using assembly 300 is also similar to the method of using instrument 200. In this regard, first and second arm assemblies 342, 343 can be operated to clamp first and second members 320, 330 onto a spinal rod 120 between adjacent pedicle screws 110a-b. Guide opening 316 guides cutting tool 350 in an axial direction to cut the rod 120, while the debris collection device 310 gathers cutting debris which can be removed from the patient along with the cut rod and assembly 300. Moreover, assembly 300 can be provided in a kit and may have a modular debris collection device 320 as described above.

Other variations of the previously described instruments and devices are contemplated. For example, as described above with respect to devices 10, 200 and 300, a guide opening for guiding an instrument may be selected for the particular cutting tool being utilized. For example, an ovular opening, such as opening 24, may be best suited for a burr or mill instrument that cuts from side-to-side in a sweeping motion, whereas a cylindrical opening, such as opening 216, may be best suited for a drill that cuts in an axial direction. Although not depicted, any of the previously described debris collection devices 10, 210, 310 can include a narrow slot that is configured to guide a saw in lieu of the herein described guide openings 24, 216, 316. In this regard, a narrow slot may extend through an upper wall and sidewalls of the respective debris collection device so that said slot can receive a saw blade so that said saw blade can cut an elongate element disposed within its restraint opening.

Also as described above, holding instruments 240 and 340 may be used to hold a debris collection device, such as devices 210 and 310, in place during and after cutting an elongate element. Such exemplary holding instruments 240, 340 respectively include forceps and vise grips. Other holding instruments, though not shown, are also contemplated. For example, a debris collection device, such as those previously described, can be connected to a snake arm that is configured to connect to an operating table and the like. In another example, first and second members, such as members 220 and 230, of a debris collection device may be connected to a vise where such vise utilizes a leadscrew to move the first and second members relative to each other and so as to securingly clamp an elongate member with said first and second members.

In addition, it should be understood that, although the debris collection devices 10, 210, and 310 are depicted as box-shaped, such debris collection devices can take on any number of different shapes provided that such devices form an interior space with sufficient volume to capture and retain debris. Thus, for example, the previously described debris collection devices can be spherical, cylindrical, triangular and the like.

Although the above methods are described in particular relation to a spinal rod, it should be understood that this is an exemplary application of devices 10, 200 and 300. Devices 10, 200 and 300 can be utilized in many other elongate member cutting applications in situ. In addition, devices 10, 200 and 300 can be utilized extracorporeally to help cut elongate members and collect debris therefrom in medical and nonmedical contexts. For example, devices 10, 200 and 300 can be used to cut pipes, conduit, electrical cables, and the like particularly where it is desirable to contain debris formed by such cutting.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A debris collection device comprising:
first and second members each having one or more walls and notches extending into one or more of said walls, the first and second members being hingedly connected and moveable relative to each other between first and second configurations wherein in the second configuration the first and second members interface so that the first and second members jointly form:
a first opening defined by the notches of the first and second members when the first and second members are in the second configuration, the first opening being configured to receive an elongate element therein such that, when the elongate element is received therein, the elongate element can extend entirely through the debris collection device from one side to another,
a second opening configured to receive a cutting instrument and that defines an axis that extends transverse to and intersects an axis defined by the first opening, and
an interior space that is defined by a floor and sidewalls extending from said floor, wherein said floor and sidewalls are comprised of the one or more walls of the first and second members.

2. The device of claim 1, wherein the first and second members include a locking mechanism that locks the first and second members in the second configuration.

3. The device of claim 1, wherein the notches extend into at least two opposing walls of the first and second members such that when the first and second members are in the second configuration the notches are adjacently disposed to form the first opening.

4. The device of claim 1, wherein, the second opening is formed by interfacing notches that extend into respective upper walls of the first and second members.

5. The device of claim 1, wherein in the second configuration, the second opening extends through an upper wall of the first member and defines an axis that intersects a base surface defined by the second member.

6. The device of claim 1, wherein the first and second members are connected to a holding instrument.

7. The device of claim 6, wherein, the holding instrument is a forceps and the first member is connected to a first arm of the forceps and the second member is connected to a second arm of the forceps.

8. The device of claim 6, wherein the holding instrument is a vise grip that includes a first arm assembly connected to the first member, a second arm assembly connected to the second member, and a locking member connected to both the first and second arm assemblies and configured to lock the first and second members in the second configuration.

9. The device of claim 1, wherein the second opening is at least partially covered by a compliant covering.

10. A debris collection device comprising:
first and second members each having a plurality of walls and being moveable relative to each other from a first configuration to a second configuration, wherein when the first and second members are in the second configuration the sidewalls of the first and second members collectively form a body defining a first opening extending through an end surface of the body and a second opening extending through the sidewalls of the body, the first opening having an axis extending transverse to an axis of the second opening and being dimensioned to receive an elongate member therein, the second opening being dimensioned to receive a cutting tool therein, the axis of the second opening intersecting a base surface within the body.

11. The device of claim 10, wherein the second opening defines an entrance into the body through an exterior surface thereof, and when the elongate member is received within the first opening, the base surface is disposed at an opposite side of the elongate member than the entrance.

12. The device of claim 10, wherein the second member includes the base surface, and the second opening extends entirely through a wall of the first member.

13. The device of claim 12, wherein the first and second members are moveable relative to each other when in the first configuration and are connected to each other via a locking mechanism when in the second configuration such that the first and second members are immoveable relative to each other while the locking mechanism remains engaged.

14. The device of claim 10, wherein the first and second members each define a portion of the base surface.

15. The device of claim 10, further comprising a holding instrument, the holding instrument being a forceps having first and second arms, the first member is connected to the first arm of the forceps and the second member is connected to the second arm of the forceps.

16. The device of claim 10, further comprising a holding instrument, the holding instrument being a vise grip that includes a first arm assembly connected to the first member, a second arm assembly connected to the second member, and a locking member connected to both the first and second arm assemblies and configured to lock the first and second members in the second configuration.

* * * * *